US010166078B2

(12) United States Patent
Sela et al.

(10) Patent No.: US 10,166,078 B2
(45) Date of Patent: Jan. 1, 2019

(54) SYSTEM AND METHOD FOR MAPPING NAVIGATION SPACE TO PATIENT SPACE IN A MEDICAL PROCEDURE (71) Applicants: Gal Sela, Toronto (CA); Dorothy Lui, Toronto (CA); Alexander Gyles Panther, Toronto (CA); Kelly Noel Dyer, Toronto (CA)

(72) Inventors: Gal Sela, Toronto (CA); Dorothy Lui, Toronto (CA); Alexander Gyles Panther, Toronto (CA); Kelly Noel Dyer, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 10 days.

(21) Appl. No.: 15/537,576

(22) PCT Filed: Jul. 21, 2015

(86) PCT No.: PCT/CA2015/050677
§ 371 (c)(1),
(2) Date: Jun. 19, 2017

(87) PCT Pub. No.: WO2017/011892
PCT Pub. Date: Jan. 26, 2017

(65) Prior Publication Data
US 2018/0263707 A1 Sep. 20, 2018

(51) Int. Cl.
A61B 34/20 (2016.01)
G06T 7/30 (2017.01)
(Continued)

(52) U.S. Cl.
CPC ............ *A61B 34/20* (2016.02); *A61B 5/0035* (2013.01); *A61B 90/36* (2016.02); *G06T 7/30* (2017.01);
(Continued)

(58) Field of Classification Search
CPC ....... A61B 34/20; A61B 5/0035; A61B 90/36; A61B 2034/2055; A61B 2034/2068;
(Continued)

(56) References Cited

U.S. PATENT DOCUMENTS 6,016,439 A * 1/2000 Acker .................. A61B 5/06
600/411
6,484,049 B1 * 11/2002 Seeley ................. A61B 5/06
600/426

(Continued)

FOREIGN PATENT DOCUMENTS

CA 2846729 9/2014

*Primary Examiner* — Peter Luong
(74) *Attorney, Agent, or Firm* — Ridout & Maybee LLP (57) ABSTRACT A medical navigation system is provided for registering a patient for a medical procedure with the medical navigation system using fiducial markers. The fiducial markers are placed on the patient prior to a 3D scan and the fiducial markers each have a target for use with a tracking system. The medical navigation system comprises a 3D scanner, a tracking system, a display, and a controller electrically coupled to the 3D scanner, the tracking system, and the display. The controller has a processor coupled to a memory. The controller is configured to: receive 3D scan data generated by the 3D scanner representative of a 3D scan of at least a portion of the patient, the 3D scan including the fiducial markers visible by the 3D scanner; load from the memory saved medical image data, the saved medical data including preoperative image data saved during a previous scan of at least a portion of the patient; receive position data from the tracking system based on the target for each of the fiducial markers; and perform a transformation mapping to create a single unified virtual coordinate space based on the 3D scan data, the position data, and the medical image data, and updating registration data of the medical navigation system based on the transformation mapping.

26 Claims, 8 Drawing Sheets (51) Int. Cl.
 *A61B 90/00* (2016.01)
 *A61B 5/00* (2006.01)
(52) U.S. Cl.
 CPC .......... *A61B 2034/2051* (2016.02); *A61B 2034/2055* (2016.02); *A61B 2034/2068* (2016.02); *A61B 2090/363* (2016.02); *G06T 2207/10028* (2013.01); *G06T 2207/10081* (2013.01); *G06T 2207/10096* (2013.01); *G06T 2207/10104* (2013.01); *G06T 2207/10116* (2013.01); *G06T 2207/10132* (2013.01)
(58) Field of Classification Search
 CPC ...... A61B 2034/2051; A61B 2090/363; G06T 7/30; G06T 2207/10132; G06T 2207/10028; G06T 2207/10116; G06T 2207/10104; G06T 2207/10096; G06T 2207/10081
 See application file for complete search history.

(56) References Cited

U.S. PATENT DOCUMENTS

| | | |
|---|---|---|
| 2002/0183608 A1 | 12/2002 | Marmulla et al. |
| 2002/0188194 A1 | 12/2002 | Cosman |
| 2003/0179856 A1 | 9/2003 | Mitschke et al. |
| 2005/0228266 A1 | 10/2005 | McCombs |

\* cited by examiner

SYSTEM AND METHOD FOR MAPPING NAVIGATION SPACE TO PATIENT SPACE IN A MEDICAL PROCEDURE

TECHNICAL FIELD

The present disclosure is generally related to neurosurgical or medical procedures, and more specifically to a system and method for mapping navigation space to patient space in a medical procedure.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

Triangulation based 3D sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, known geometric/triangulation equations are utilized to determine distance to the imaged object. The main differences among the various triangulation methods known in the art lie in the method of projection as well as the type of light projected, typically structured light, and in the process of image decoding to obtain three dimensional data.

A 3D sensor system may be contemplated as a novel extension of a surgical navigation systems. One popular triangulation based 3D sensor system is created by Mantis Vision, which utilizes a single frame structured light active triangulation system to project infrared light patterns onto an environment. To capture 3D information, a projector overlays an infrared light pattern onto the scanning target. Then a digital camera and a depth sensor, synched to the projector, captures the scene with the light reflected by the object. The technology works even in complete darkness, since it includes its own illumination; in bright environments the quality of the resulting image depends on the hardware used.

During a medical procedure, navigation systems require a registration to transform between the physical position of the patient in the operating room and the volumetric image set (e.g., MRI/CT) being navigated to. Conventionally, this registration is done to the position of a reference tool, which is visible by the tracking system and stays fixed in position and orientation relative to the patient throughout the procedure.

This registration is typically accomplished through correspondence touch points (e.g., either fiducial or anatomic points). Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position. Another conventional approach to collecting the touch points includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the conventional approaches to registration discussed above include a stylus that needs to remain visible to the tracking system, which not necessarily possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult if not possible to be completed again during surgery.

Therefore, there is a need for an improved system and method for mapping navigation space to patient space in a medical procedure.

SUMMARY

One aspect of the present disclosure provides a medical navigation system for registering a patient for a medical procedure with the medical navigation system using fiducial markers. The fiducial markers are placed on the patient prior to a 3D scan and the fiducial markers each have a target for use with a tracking system. The medical navigation system comprises a 3D scanner, a tracking system, a display, and a controller electrically coupled to the 3D scanner, the tracking system, and the display. The controller has a processor coupled to a memory. The controller is configured to: receive 3D scan data generated by the 3D scanner representative of a 3D scan of at least a portion of the patient, the 3D scan including the fiducial markers visible by the 3D scanner; load from the memory saved medical image data, the saved medical data including preoperative image data saved during a previous scan of at least a portion of the patient; receive position data from the tracking system based on the target for each of the fiducial markers; and perform a transformation mapping to create a single unified virtual coordinate space based on the 3D scan data, the position data, and the medical image data, and update registration data of the medical navigation system based on the transformation mapping.

Another aspect of the present disclosure provides a method of registering a patient for a medical procedure with a medical navigation system using fiducial markers visible by a three dimensional (3D) scanner of the medical navigation system. The fiducial markers are placed on the patient prior to a 3D scan and the fiducial markers each have a target for use with a tracking system of the medical navigation system. The method comprises generating and receiving 3D scan data from the 3D scanner representative of a 3D scan of at least a portion of the patient, the 3D scan including the fiducial markers visible by the 3D scanner; loading saved medical image data, the saved medical data including preoperative image data saved during a previous scan of at least a portion of the patient; generating and receiving position data from the tracking system based on the target for each of the fiducial markers; and performing a transformation mapping to create a single unified virtual coordinate space based on the 3D scan data, the position data, and the medical image data, and updating registration data of the medical navigation system based on the transformation mapping.

The target may be usable with a pointer tool and the generating and receiving position data from the tracking system includes a location of the pointer tool when a tip of the pointer tool is placed on the target for each of the fiducial markers.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

The present disclosure is generally related to medical procedures, neurosurgery, and minimally invasive port-based surgery in specific.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

Figure 1:
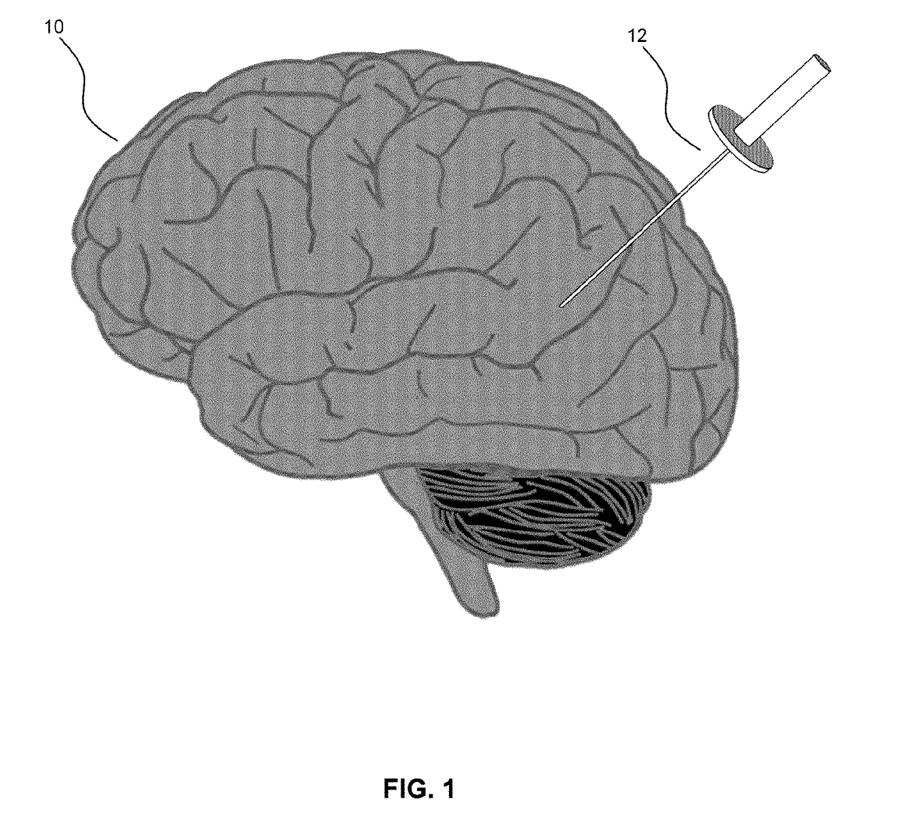
FIG. 1 illustrates the insertion of an access port into a human brain, for providing access to internal brain tissue during a medical procedure.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments would then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Figure 2:
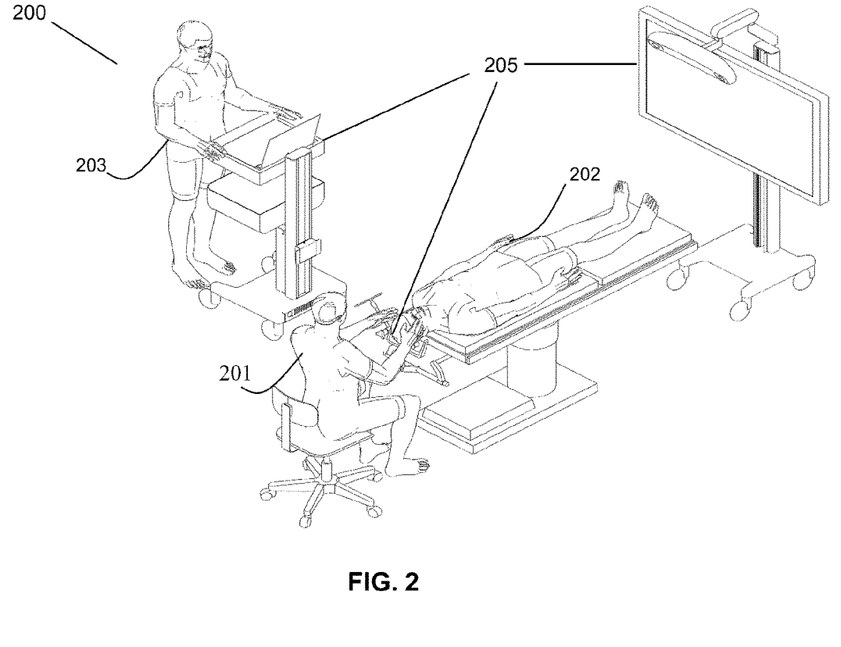
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
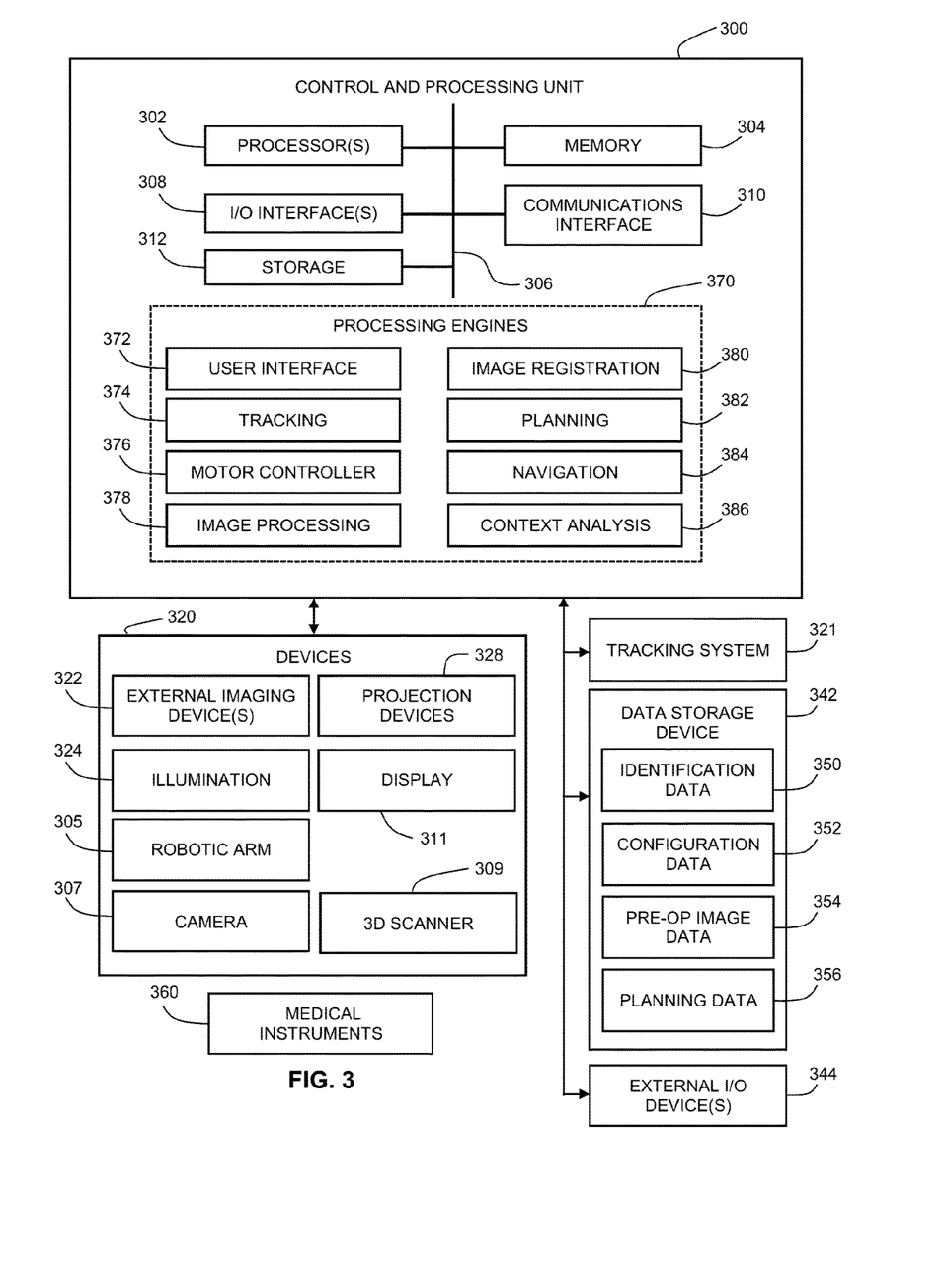
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, a 3D scanner 309, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using optical tracking instead of infrared cameras.

Figure 4A:
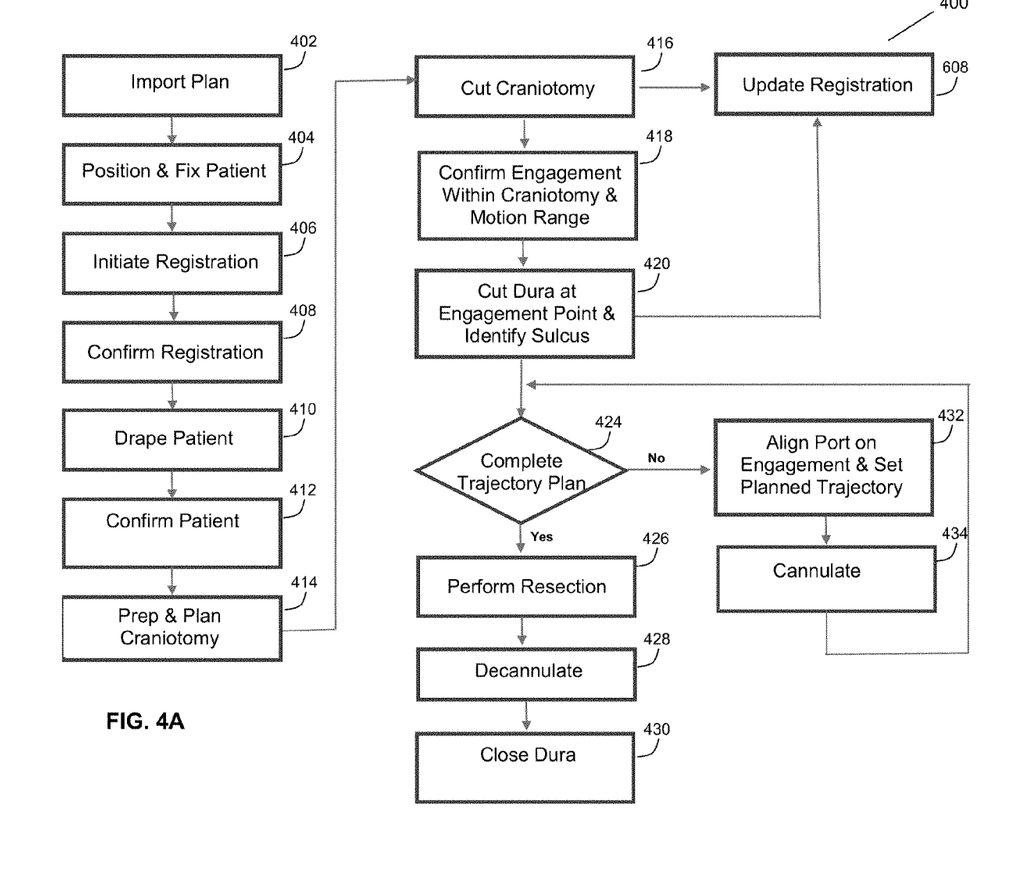
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by a computer or controller forming part of the equipment tower.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities to the patient in physical space.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT to patient in physical space.

Figure 4B:
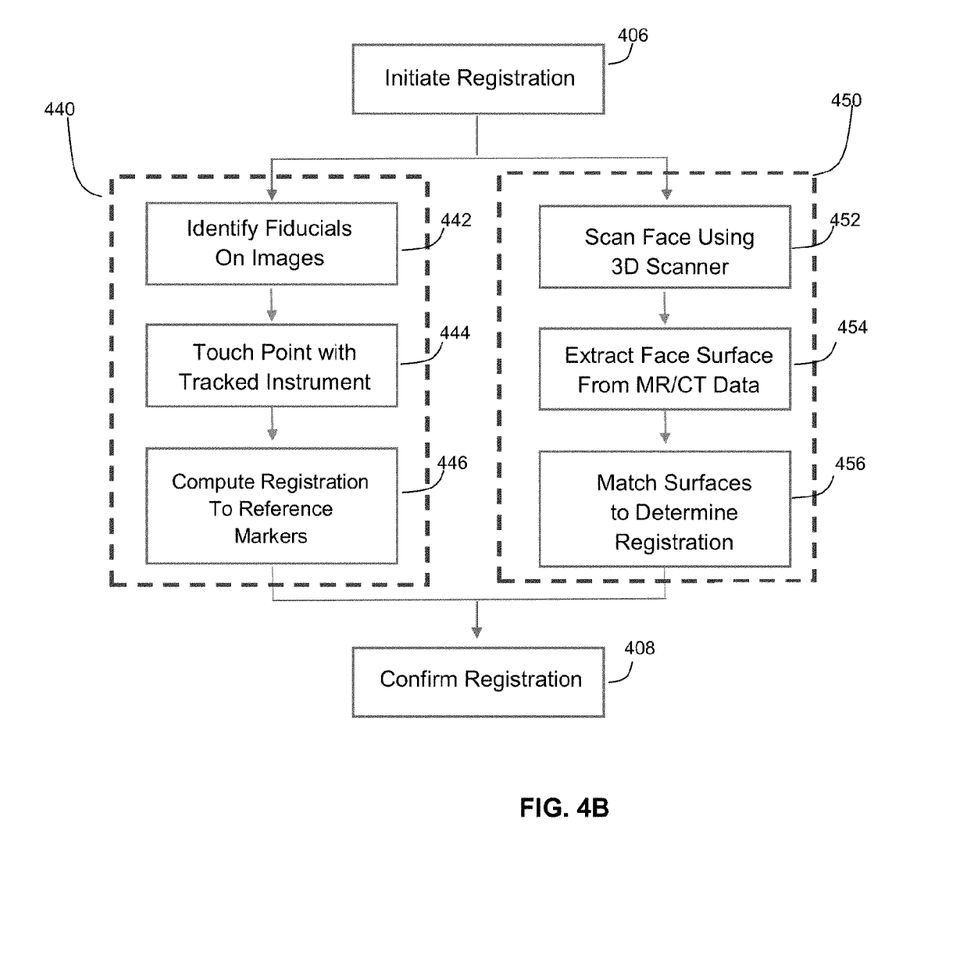
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450), which may be applied to aspects of the present disclosure. The block 450 is presented to show an alternative approach. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

Figure 5:
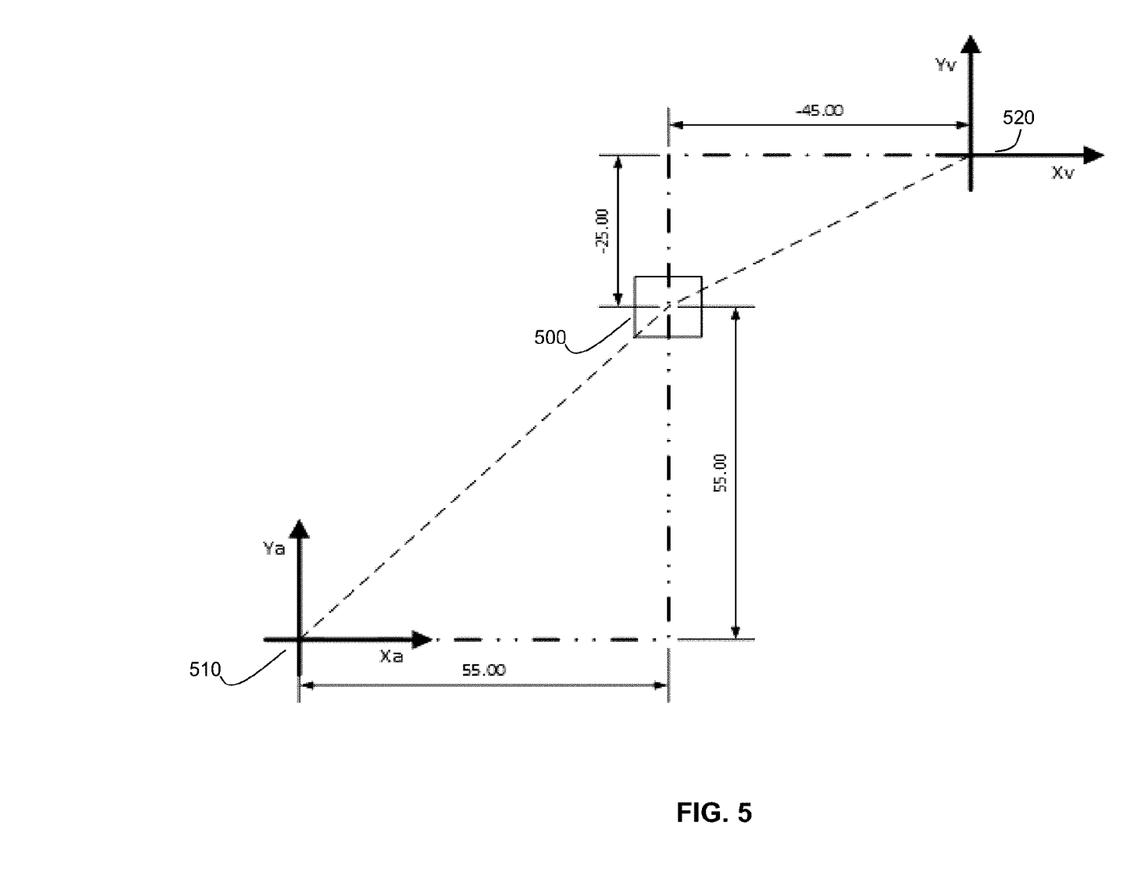
FIG. 5 illustrates a flow chart describing the use of multiple patient reference markers for registration.

Referring now to FIG. 5, a registration process, similar to that which may be used in block 456 of FIG. 4B, is shown for creating a common coordinate space composed of amalgamated virtual and actual coordinate spaces. The common coordinate space may be composed of both an actual coordinate space and a virtual coordinate space, where the actual coordinate space contains actual objects that exist in space and the virtual coordinate space contains virtual objects that are generated in a virtual space. The common coordinate space containing both the aforementioned actual and virtual objects may be produced as follows.

In order to form a common coordinate space composed of the amalgamated virtual and actual coordinate spaces, the two spaces may be coupled with a "common reference coordinate", having a defined position that can be located in both the actual and virtual coordinate spaces. An example of such a common reference coordinate 500 and actual and virtual coordinate space origins, 510 and 520, are provided in FIG. 5. Once the common reference coordinate position is acquired in both spaces they can be used to correlate the position of any point in one coordinate space to the other. The correlation is determined by equating the locations of the common reference coordinate in both spaces and solving for an unknown translation variable for each degree of freedom defined in the two coordinate spaces. These translation variables may then be used to transform a coordinate element of a position in one space to an equivalent coordinate element of a position in the other. An example correlation can be derived from the diagram in FIG. 5 depicting a two dimensional coordinate space. In FIG. 5, the common reference coordinates 500 position is determined relative to the actual coordinate space origin 510 and the virtual coordinate space origin 520. The common reference coordinates positions can be derived from the diagram as follows:

$$(X_{cra}, Y_{cra})=(55, 55)$$

and $$(X_{crv}, Y_{crv})=(-25, -45)$$

Where the subscript "cra" denotes the common reference coordinate position relative to the actual coordinate space origin and the subscript "crv" denotes the common reference coordinate position relative to the virtual coordinate space origin. Utilizing a generic translation equation describing any points $((Y_a, X_a)$ and $(Y_v, X_v))$, where the subscript "a" denotes the coordinates of a point relative to the actual coordinate space origin 510, and the subscript "v" denotes the coordinate of a point relative to the virtual coordinate space origin 520, we can equate the individual coordinates from each space to solve for translation variables $((Y_T, X_T))$, where the subscript "T" denotes the translation variable as shown below.

$$Y_a=Y_v+Y_T$$

$$X_a=X_v+X_T$$

Now substituting the derived values of our points from FIG. 5 we can solve for the translation variable.

$$55=-45+Y_T$$

$$100=Y_T$$

and $$55=-25+X_T$$

$$80=X_T$$

Utilizing this translation variable, any point ((i.e. $(Y_v, X_v)$) in the virtual coordinate space may be transformed into an equivalent point in the actual coordinate space through the two generic transformation equations provided below. It should be noted that these equations can be rearranged to transform any coordinate element of a position from the actual coordinate space into an equivalent coordinate element of a position in the virtual coordinate space as well.

$$Y_a=Y_v+100$$

and $$X_a=X_v+80$$

This will allow both the virtual and actual objects respective positions to therefore be defined in both the actual and virtual coordinate spaces simultaneously. Once the correlation is determined the actual and virtual coordinate spaces become coupled and the result in the formation of a common coordinate space that may be used to register virtual and actual objects. It should be noted that these virtual and actual objects can be superimposed in the common coordinate space (e.g., they can occupy the same coordinates simultaneously).

According to one aspect of the present application, using a handheld three dimensional (3D) surface scanner, such as the 3D scanner 309, a full or nearly full array scan of a patient's surface can be achieved, as opposed to 1D line or a 2D grid of point depths with the conventional approaches. This may provide an order of magnitude greater point information than the surface tracing methods used in conventional approaches. Using a dense point cloud provided by the 3D scanner 309, this point cloud may be mapped to the extracted surface of the MR/CT volumetric scan data (e.g., the pre-op image data 354) to register the patient's physical position to the volumetric data. The tracking system 321 (e.g., part of the navigation system 200) has no reference to the point cloud data. Therefore a tool or marker may be provided that is visible to both the tracking system 321 and the 3D scanner 309. A transformation between the tracking system's camera space and the 3D scanner space may be identified so that the point cloud provided by the 3D scanner 309 and the tracking system 321 can be registered to the patient space. A transformation similar to or based on the transformation described in connection with FIG. 5 may be used.

One aspect of the present application provides an approach, compared to conventional solutions, that aims to register the patient's current surgical position to the imaging data by placing a series of markers on the patient's head that are visible by a handheld 3D scanner, such as the 2D scanner 309. Following the placement of these targets, the 3D scanner is used to collect a surface extraction of the head where the location of the targets can be identified in the 3D scanner space. To map this space to the imaging data space, the extracted surface can be fitted to the imaging volume surface extraction. Then, the marker locations can be identified in the imaging space and shown to the user for touch point data collection to identify the markers in the medical navigation space. In another example, the markers may be directly observable by the tracking system.

The approach of the present application may be similar to touch point fiducial registration but eliminates the need for tedious placement and imaging of the patient with fiducial markers that are visible in the imaging modality during preoperative imaging. In another example, following the registration of the 3D scanner extracted surface and the imaging volume extracted surface, anatomical features in the imaging data can be automatically extracted. Then, these locations can be identified by touching the navigation tool to each location.

The approaches mentioned above may be useful for recover points, pin-less registration, continuous pinless registration. Further, a patient may not need a scan on the day of the medical procedure resulting in eliminating some of the radiation dosage. Placement of the markers on the patient may be done in the operating room or by technical team preparing the patient for surgery. The markers or fiducial stickers could also be a line, other material, or any suitable fiducial marker.

Figure 6:
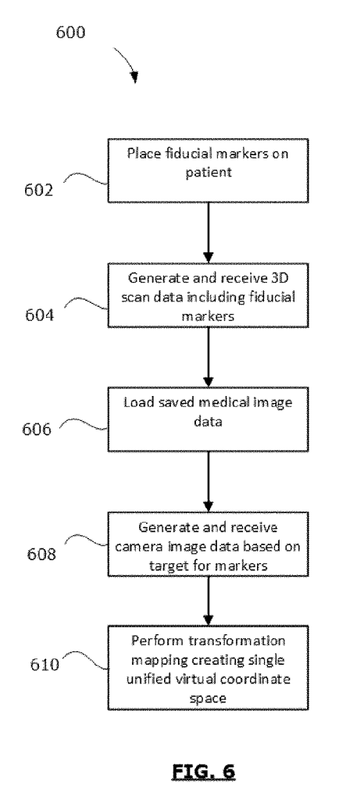
FIG. 6 is a flow chart illustrating a method of registering a patient for a medical procedure with a medical navigation system.
Figure 7:
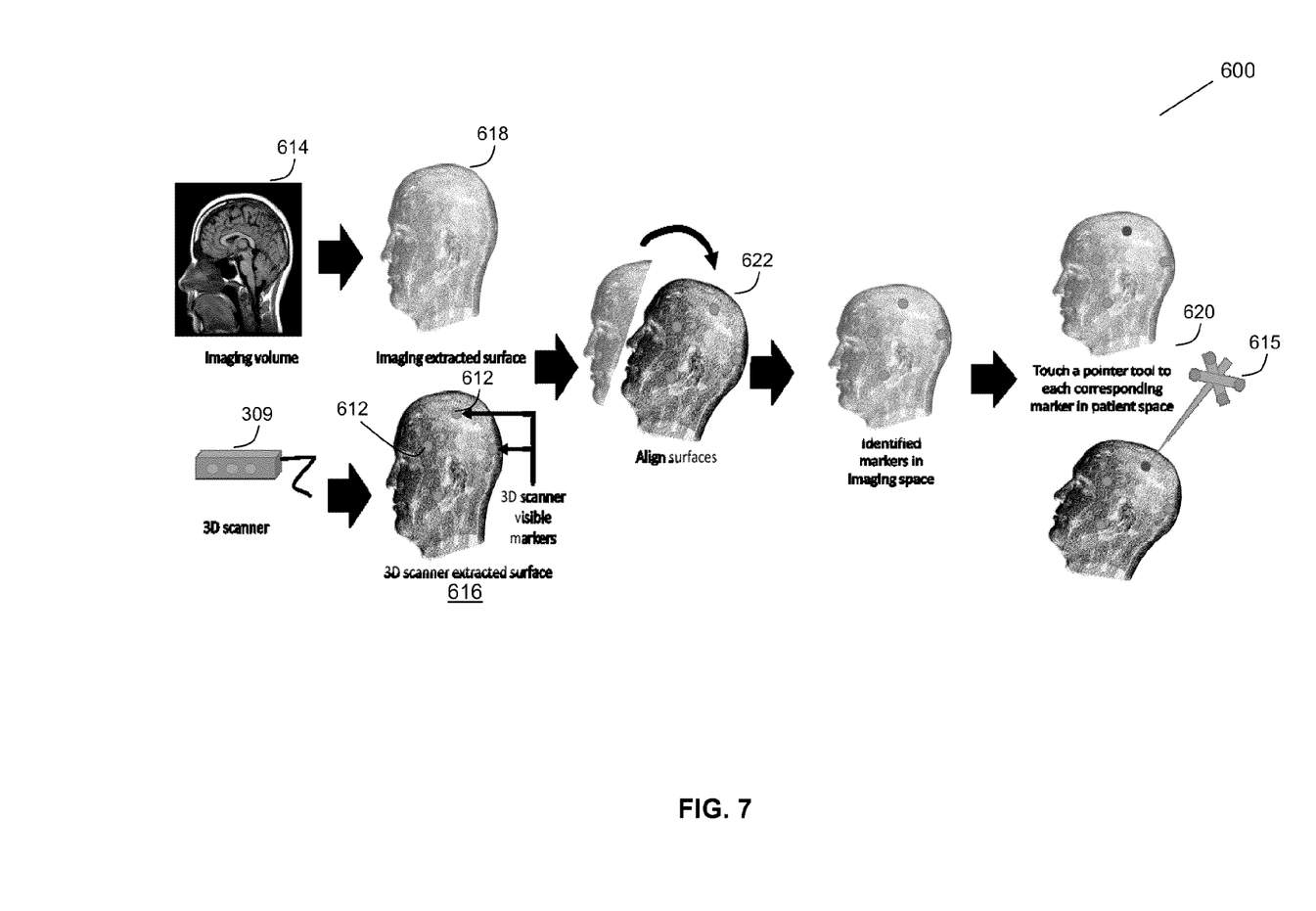
FIG. 7 is another flow chart illustrating a method of registering a patient for a medical procedure with a medical navigation system.

Referring to FIG. 6, a flow chart is shown illustrating a method 600 of registering a patient for a medical procedure with a medical navigation system, such as the medical navigation system 205. Referring to FIG. 7, another flow chart is shown illustrating the method 600 of registering a patient for a medical procedure with a medical navigation system in a more graphical fashion. FIGS. 6 and 7 will now be discussed concurrently.

The medical navigation system 205 may be used for registering a patient for a medical procedure with the medical navigation system using fiducial markers. The fiducial markers may be placed on the patient prior to a 3D scan and the fiducial markers may each have a target for use with a tool, such as a pointer tool. In another example, the fiducial markers may be directly observable by the tracking system and no pointer tool may be needed. The medical navigation system may include a 3D scanner, such as 3D scanner 309, a tracking system, such as tracking system 321, a display, such as display 311, and a controller (e.g., processing unit 300) electrically coupled to the 3D scanner 309, the tracking system 321, and the display 311. The controller may include a processor (e.g., processor 302) coupled to a memory (e.g., memory 304) and the controller may be configured to execute the method 600.

The method 600 may be a method of registering a patient for a medical procedure with a medical navigation system using fiducial markers visible by a three dimensional (3D) scanner of the medical navigation system. The fiducial markers may be placed on the patient prior to a 3D scan and the fiducial markers may each have a target usable with a pointer tool visible by a tracking system of the medical navigation system.

At a first block 602, fiducial markers are placed on the patient, indicated by reference 612 in FIG. 7. In one example, the patient has at least three fiducial markers placed on the patient after the previous scan during which the preoperative image data was saved but prior to the 3D scan. In the example shown in FIG. 7, four fiducial markers have been placed on the patient's head. In another example, at least three fiducial markers may be placed on the patient on an area of the patient corresponding to the saved medical image data (e.g., if the saved medical image data pertains to a patient's head, the fiducial markers may be placed in an appropriate area of the head where the medical procedure will be performed). In one example, the fiducial markers include fiducial stickers. The fiducial markers may include a retro-reflective area visible by the 3D scanner and the preoperative image data, indicated by reference 614 in FIG. 7, does not have to include the fiducial markers. In one example, the fiducial markers may each have a target that is visible by the tracking system. In one example, the target includes a divot for receiving the tip of the pointer, indicated by reference 615 in FIG. 7.

At a second block 604, the method 600 generates and receives 3D scan data from the 3D scanner 309 representative of a 3D scan of at least a portion of the patient. The 3D scan includes the fiducial markers visible by the 3D scanner. The 3D scanner extracted surface is indicated by reference 616 in FIG. 7.

Next, at a block 606, the method 600 loads saved medical image data, which includes saved medical data including preoperative image data saved during a previous scan of at least a portion of the patient. At this stage, or later one, the method 600 may also extract an imaging surface from the imaging volume of the saved medical image data, indicated by reference 618 in FIG. 7. In one example, the saved medical image data includes at least one of magnetic resonance (MR) coordinates taken from a MR scan or computed tomography (CT) coordinates taken from a CT scan. The preoperative image data may include data from at least one of computerized tomography (CT) images, magnetic resonance imaging (MRI) images, positron emission topography (PET) images, contrast-enhanced CT images, X-ray images, or ultrasound images.

Next at a block 608, the method 600 generates and receives position data from the tracking system based on the target for each of the fiducial markers. In the example where the target includes a divot for a pointer tool, the generating and receiving position data from the tracking system includes a location of the pointer tool when a tip of the pointer tool is placed on the target for each of the fiducial markers, indicated by reference 620 in FIG. 7. In other words, the surgeon or technician performing the method 600 holds the pointer tool with a tip of the pointer tool in each of the divots so that the tracking system can register the position of the pointer tool by observing the positions of the markers on the pointer tool, and consequently the position of the target is known. While the example of an optical tracking system is used, the tracking system may include any one of an optical tracking system, an electromagnetic tracking system, and a radio frequency tracking system with appropriate markers being substituted.

Next, at a block 610, the method 600 performs a transformation mapping to create a single unified virtual coordinate space based on the 3D scan data, the position data, and the medical image data, and updates registration data of the medical navigation system based on the transformation mapping. In one example, the transformation mapping first includes a surface matching calculation using a 3D scanner point cloud based on the 3D scan data and at least one of the MR and CT coordinates, indicated by reference 622 in FIG. 7. The transformation mapping may further include registering the tracking system to create a single unified virtual coordinate space for the 3D scanner point cloud, at least one of the MR and CT coordinates, and the position data from the tracking system based on the locations of the markers, for example when the tip of the pointer tool is placed on the targets. In one example, registering the tracking system to the aligned surfaces from the 3D scanner point cloud based on the 3D scan data and at least one of the MR and CT coordinates may be performed using a point wise correspondence approach.

While the blocks of FIG. 6 are shown in a particular order for the purpose of example, the blocks 602, 604, 606, 608, and 610 need not be executed in the exact order shown and suitable modifications may be made to this order.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A method of registering a patient for a medical procedure with a medical navigation system using fiducial markers visible by a three dimensional (3D) scanner of the medical navigation system, the fiducial markers placed on the patient prior to a 3D scan and the fiducial markers each having a target for use with a tracking system of the medical navigation system, the 3D scanner operating in a different coordinate space relative to the tracking system, the method comprising:
    obtaining 3D scan data from the 3D scanner representative of a 3D scan of at least a portion of the patient, the 3D scan including the fiducial markers visible by the 3D scanner, the 3D scan data being in a 3D scanner coordinate space;
    obtaining saved medical image data, the saved medical image data including preoperative image data saved during a previous scan of at least a portion of the patient;
    obtaining position data from the tracking system based on the target for each of the fiducial markers, the position data being in a tracking coordinate space independent from the 3D scanner coordinate space;
    performing a transformation mapping to create a single unified virtual coordinate space based on the 3D scan data, the position data, and the medical image data, the transformation mapping including: performing a first mapping to map one of the 3D scan data, the position data, and the medical image data to a second of the 3D scan data, the position data, and the medical image data; and
    performing a second mapping to map a third of the 3D scan data, the position data, and the medical image data to the first mapping; and
    updating registration data of the medical navigation system based on the transformation mapping.

2. The method according to claim 1, wherein the target is usable with a pointer tool and the position data from the tracking system includes a location of the pointer tool when a tip of the pointer tool is placed on the target for each of the fiducial markers.

3. The method according to claim 2, wherein the patient has at least three fiducial markers placed on the patient after the previous scan during which the preoperative image data was saved but prior to the 3D scan and the use of the pointer tool.

4. The method according to claim 2, wherein the saved medical image data includes at least one of magnetic resonance (MR) coordinates taken from a MR scan and computed tomography (CT) coordinates taken from a CT scan.

5. The method according to claim 4, wherein the transformation mapping includes a surface matching approach using a 3D scanner point cloud based on the 3D scan data and at least one of the MR and CT coordinates.

6. The method according to claim 5, wherein the transformation mapping further includes registering the tracking system to create the single unified virtual coordinate space for the 3D scanner point cloud, at least one of the MR and CT coordinates, and the position data from the tracking system based on the locations of the pointer tool when the tip is placed on the targets.

7. The method according to claim 1, wherein the preoperative image data includes data from at least one of computerized tomography (CT) images, magnetic resonance imaging (MRI) images, positron emission topography (PET) images, contrast-enhanced CT images, X-ray images, and ultrasound images.

8. The method according to claim 1, further comprising, prior to obtaining 3D scan data:
    placing at least three fiducial markers on an area of the patient corresponding to the saved medical image data.

9. The method according to claim 1, wherein the fiducial markers include fiducial stickers.

10. The method according to claim 1, wherein the fiducial markers include a retro-reflective area visible by the 3D scanner.

11. The method according to claim 1, wherein the preoperative image data does not include fiducial markers.

12. The method according to claim 2, wherein the target includes a divot for receiving the tip of the pointer.

13. The method according to claim 1, wherein the tracking system includes any one of an optical tracking system, an electromagnetic tracking system, and a radio frequency tracking system.

14. A medical navigation system for registering a patient for a medical procedure with the medical navigation system using fiducial markers, the fiducial markers placed on the patient prior to a 3D scan and the fiducial markers each having a target for use with a tracking system, the 3D scanner operating in a different coordinate space relative to the tracking system, the medical navigation system comprising:
    a 3D scanner;
    the tracking system;
    a display; and a controller electrically coupled to the 3D scanner, the tracking system, and the display, the controller having a processor coupled to a memory, the controller being configured to:

receive 3D scan data generated by the 3D scanner representative of a 3D scan of at least a portion of the patient, the 3D scan including the fiducial markers visible by the 3D scanner, the 3D scan data being in a 3D scanner coordinate space;

load from the memory saved medical image data, the saved medical image data including preoperative image data saved during a previous scan of at least a portion of the patient;

receive position data from the tracking system based on the target for each of the fiducial markers, the position data being in a tracking coordinate space independent from the 3D scanner coordinate space; and perform a transformation mapping to create a single unified virtual coordinate space based on the 3D scan data, the position data, and the medical image data, the transformation mapping including: performing a first mapping to map one of the 3D scan data, the position data, and the medical image data to a second of the 3D scan data, the position data, and the medical image data; and performing a second mapping to map a third of the 3D scan data, the position data, and the medical image data to the first mapping; and updating registration data of the medical navigation system based on the transformation mapping.

15. The medical navigation system according to claim 14, wherein the target is usable with a pointer tool and the position data from the tracking system includes a location of the pointer tool when a tip of the pointer tool is placed on the target for each of the fiducial markers.

16. The medical navigation system according to claim 15, wherein the patient has at least three fiducial markers placed on the patient after the previous scan during which the preoperative image data was saved but prior to the 3D scan and the use of the pointer tool.

17. The medical navigation system according to claim 15, wherein the saved medical image data includes at least one of magnetic resonance (MR) coordinates taken from a MR scan and computed tomography (CT) coordinates taken from a CT scan.

18. The medical navigation system according to claim 17, wherein the transformation mapping includes a surface matching approach using a 3D scanner point cloud based on the 3D scan data and at least one of the MR and CT coordinates.

19. The medical navigation system according to claim 18, wherein the transformation mapping further includes registering the tracking system to create a single unified virtual coordinate space for the 3D scanner point cloud, at least one of the MR and CT coordinates, and the position data from the tracking system based on the locations of the pointer tool when the tip is placed on the targets.

20. The medical navigation system according to claim 14, wherein the preoperative image data includes data from at least one of computerized tomography (CT) images, magnetic resonance imaging (MRI) images, positron emission topography (PET) images, contrast-enhanced CT images, X-ray images, and ultrasound images.

21. The medical navigation system according to claim 14, wherein, prior to receiving the 3D scan data, at least three fiducial markers are placed on an area of the patient corresponding to the saved medical image data.

22. The medical navigation system according to claim 14, wherein the fiducial markers include fiducial stickers.

23. The medical navigation system according to claim 14, wherein the fiducial markers include a retro-reflective area visible by the 3D scanner.

24. The medical navigation system according to claim 14, wherein the preoperative image data does not include fiducial markers.

25. The medical navigation system according to claim 15, wherein the target includes a divot for receiving the tip of the pointer tool.

26. The medical navigation system according to claim 14, wherein the tracking system includes any one of an optical tracking system having a camera, an electromagnetic tracking system having an antenna, and a radio frequency tracking system having an antenna.

* * * * *